United States Patent
Le et al.

(10) Patent No.: US 8,453,490 B2
(45) Date of Patent: Jun. 4, 2013

(54) DROP TEST DEVICE

(75) Inventors: Yin Le, Shenzhen (CN); Yu-Lin Liu, Shenzhen (CN); Qiang Zhang, Shenzhen (CN)

(73) Assignees: Hong Fu Jin Precision Industry (ShenZhen) Co., Ltd., Shenzhen (CN); Hon Hai Precision Industry Co., Ltd., New Taipei (TW)

( * ) Notice: Subject to any disclaimer, the term of this patent is extended or adjusted under 35 U.S.C. 154(b) by 270 days.

(21) Appl. No.: 12/981,215

(22) Filed: Dec. 29, 2010

(65) Prior Publication Data

US 2012/0024040 A1     Feb. 2, 2012

(30) Foreign Application Priority Data

Jul. 29, 2010   (CN) .......................... 2010 1 0240071

(51) Int. Cl.
    *G01N 3/30*   (2006.01)
(52) U.S. Cl.
    USPC ........................ 73/12.06; 73/12.13

(58) Field of Classification Search
    USPC ................... 73/12.06, 12.13, 12.14
    See application file for complete search history.

(56) References Cited

U.S. PATENT DOCUMENTS

| | | | | |
|---|---|---|---|---|
| 5,214,953 | A * | 6/1993 | Nish et al. | 73/1.74 |
| 6,807,841 | B1 * | 10/2004 | Chen et al. | 73/12.06 |
| 7,243,526 | B2 * | 7/2007 | Pringle | 73/12.09 |
| 7,900,499 | B2 * | 3/2011 | Zhang | 73/12.13 |
| 7,973,672 | B2 * | 7/2011 | Holsomback | 340/686.1 |
| 2006/0266009 | A1 * | 11/2006 | Kawamura | 53/469 |

* cited by examiner

*Primary Examiner* — Max Noori
(74) *Attorney, Agent, or Firm* — Altis Law Group, Inc.

(57) ABSTRACT

A drop test device for testing the strength of a product includes an operating platform and a hanging mechanism. The operating platform includes a bottom board, a pillar substantially perpendicularly connected to the bottom board and a support member rotatably secured on the pillar. The hanging mechanism is mounted to the pillar, and includes a clamp member for positioning the product. The product is sandwiched by the clamp member so an arris of the product abuts the support member. The support plate is rotated away from the product, so the product can be disengaged from the clamp member and dropped towards the bottom board.

14 Claims, 4 Drawing Sheets

DROP TEST DEVICE

BACKGROUND

1. Technical Field

The present disclosure relates to drop test devices, and particularly to a drop test device for testing a strength of a product.

2. Description of Related Art

Electronic apparatuses, such as computers, are contained in a metal case. For example, a computer system is received in a computer enclosure, which is usually made of steel plates. When the computer enclosure is transported, carelessness may allow the computer enclosure to be dropped. The corners of a plate are the most vulnerable portions. When a corner of a plate of a computer enclosure lands first, the corner is easily deformed and the computer system is damaged. Therefore, the corner of the plate should be strong enough to avoid deformation. To assure the corners are strong enough, the strength of the corners of the plate need to be tested. However, it is not easy to test the strength of the corners because it is difficult to position the plate to have the corner of the plate land first when the plate drops.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
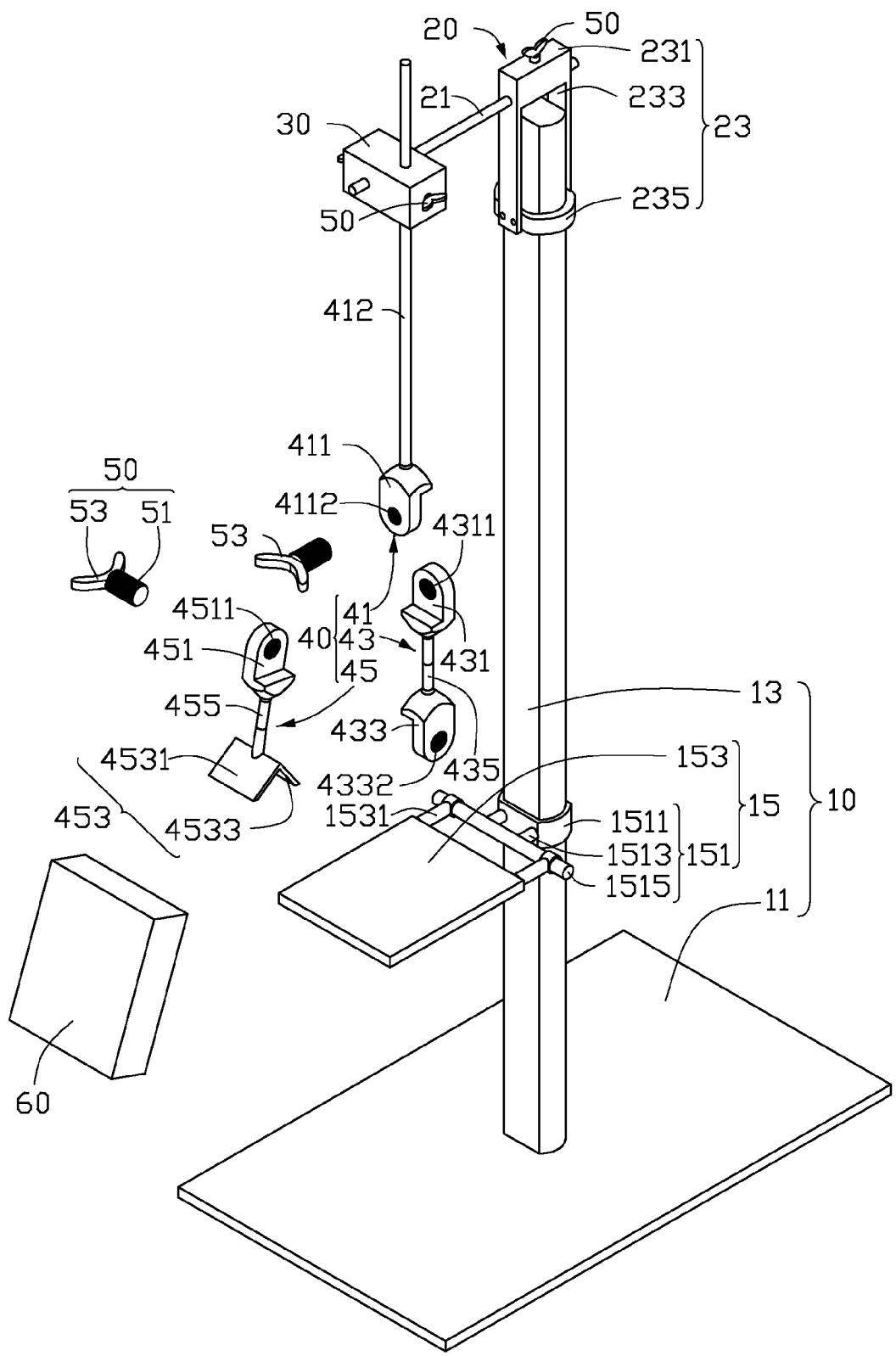
FIG. 1 is an exploded, isometric view of a drop test device in accordance with an embodiment.
Figure 2:
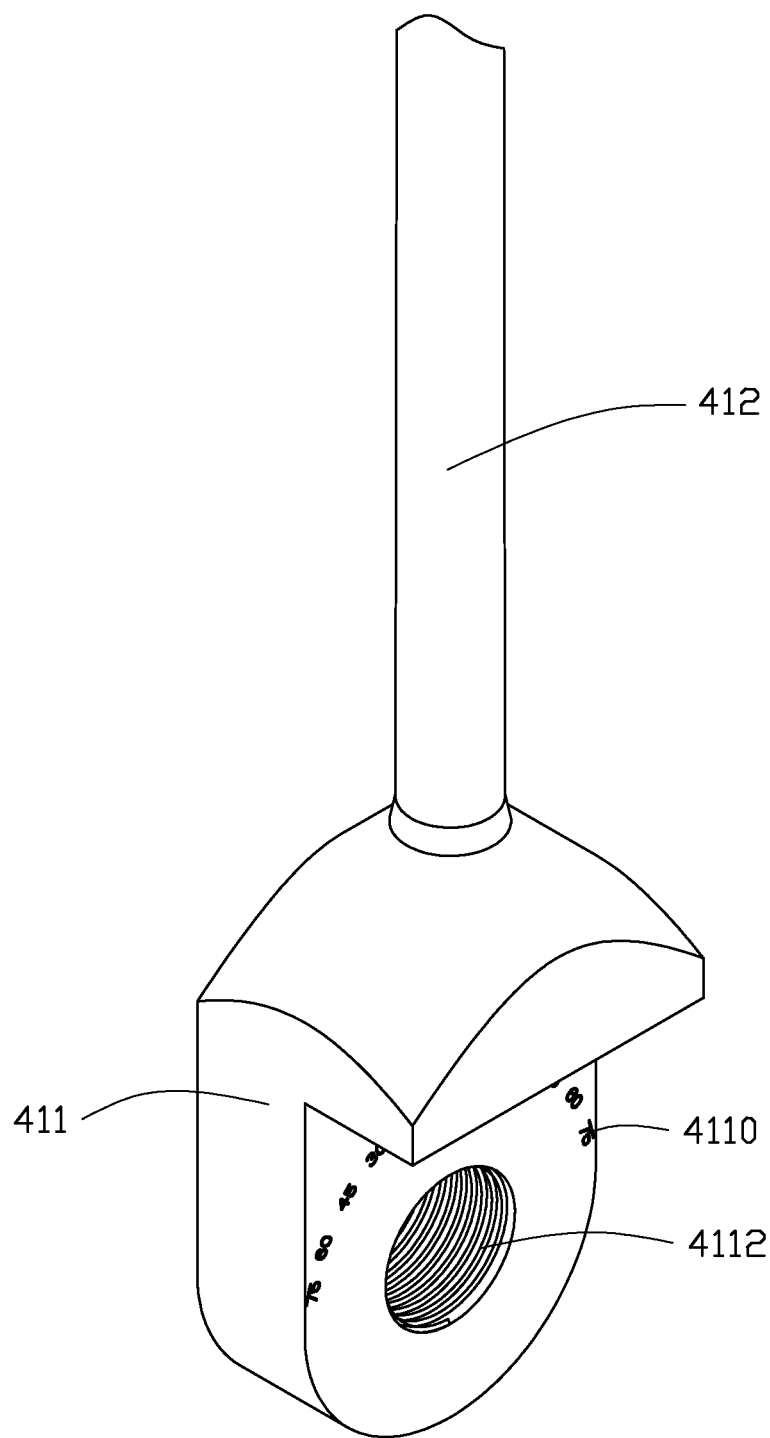
FIG. 2 is a partially isometric view of a first part of FIG. 1.

Referring to FIGS. 1 and 2, a drop test device in accordance with an embodiment includes an operating platform 10, a securing member 20 mounted on the operating platform 10, a connecting member 30, a hanging mechanism 40 secured to the connecting member 30, and a number of pivoting pins 50.

The operating platform 10 includes a bottom board 11, a pillar 13 connected to the bottom board 11, and a support member 15 rotatably secured to the pillar 13. In one embodiment, the bottom board 11 is substantially rectangle, and the pillar 13 is substantially perpendicular to the bottom board 11. The support member 15 includes a fastening portion 151 and a support plate 153 secured to the fastening portion 151. The fastening portion 151 includes a ring 1511 surrounding the pillar 13, two pins 1513 connected to the ring 1511, and a shaft 1515 connected to the two pins 1513. Two arms 1531 extend from an end of the support plate 153, and are rotatably secured to the shaft 1515.

The securing member 20 includes a frame 23, and a post 21 moveably secured to the connecting member 30. The frame 23 includes a securing portion 231, two legs 233 extending from the two opposite ends of the securing portion 231, and a loop 235 surrounding the pillar 13. One of the pivoting pins 50 is moveably attached to the securing portion 231. Both of the pivoting pins 50 are moveably attached to the two opposite sides of the connecting member 30, for allowing the connecting member 30 to move.

The hanging mechanism 40 includes a first part 41, a second part 43 and a third part 45. The first part 41 includes a first pole 412 moveably secured to the connecting member 30, and a first angle adjuster 411 connected to an end of the first pole 412. The first angle adjuster 411 can be rotated to different angles, so that the product 60 can be dropped from different angles that are formed by the product 60 and the support plate 153. A number of graduations 4110 are located on the first angle adjuster 411, for noting the angle of the second part 43. A pivot hole 4112 with inner screw (not labeled) is defined in first angle adjuster 411. In some embodiments, the number of graduations 4110 can be etched onto the first angle adjuster 411.

The second part 43 includes a pivoting portion 431, a second angle adjuster 433, and a second pole 435 between the pivoting portion 431 and the second angle adjuster 433. A mounting hole 4311 is defined in the pivoting portion 431, corresponding to the pivot hole 4112, and an arrowhead (not shown) is located on the pivoting portion 431, for showing the graduations 4110 of the first angle adjuster 411. In one embodiment, the second angle adjuster 433 has a same configuration as the first angle adjuster 411, and a number of graduations (not shown) are located on the second angle adjuster 433, for noting the angle of the third part 45. A pivot slot 4332 with an inner screw is defined in the second angle adjuster 433. In some embodiments, the arrowhead can be etched onto the pivoting portion 431

The third part 45 includes a fixing portion 451 attached to the second angle adjuster 433, a clamp member 453, and a third pole 455 between the second angle adjuster 433 and the clamp member 453. An arrowhead (not shown) is labeled on the fixing portion 451, for showing the graduations of the second angle adjuster 433. A fixing hole 4511 is defined in the fixing portion 451, corresponding to the pivot slot 4332. The clamp member 453 includes a first piece 4531 and a second piece 4533 connected to the first piece 4531. The clamp member 453 is for hanging the product 60 thereon to test the strength of the product 60. In one embodiment, the first piece 4531 is substantially perpendicular to the second piece 4533, and the third pole 455 is connected to a joint of the first and second pieces 4531, 4533.

Each pivoting pin 50 includes a screw post 51 and a head 53 connected to the screw post 51. In one embodiment, the head 53 is V-shaped.

Figure 3:
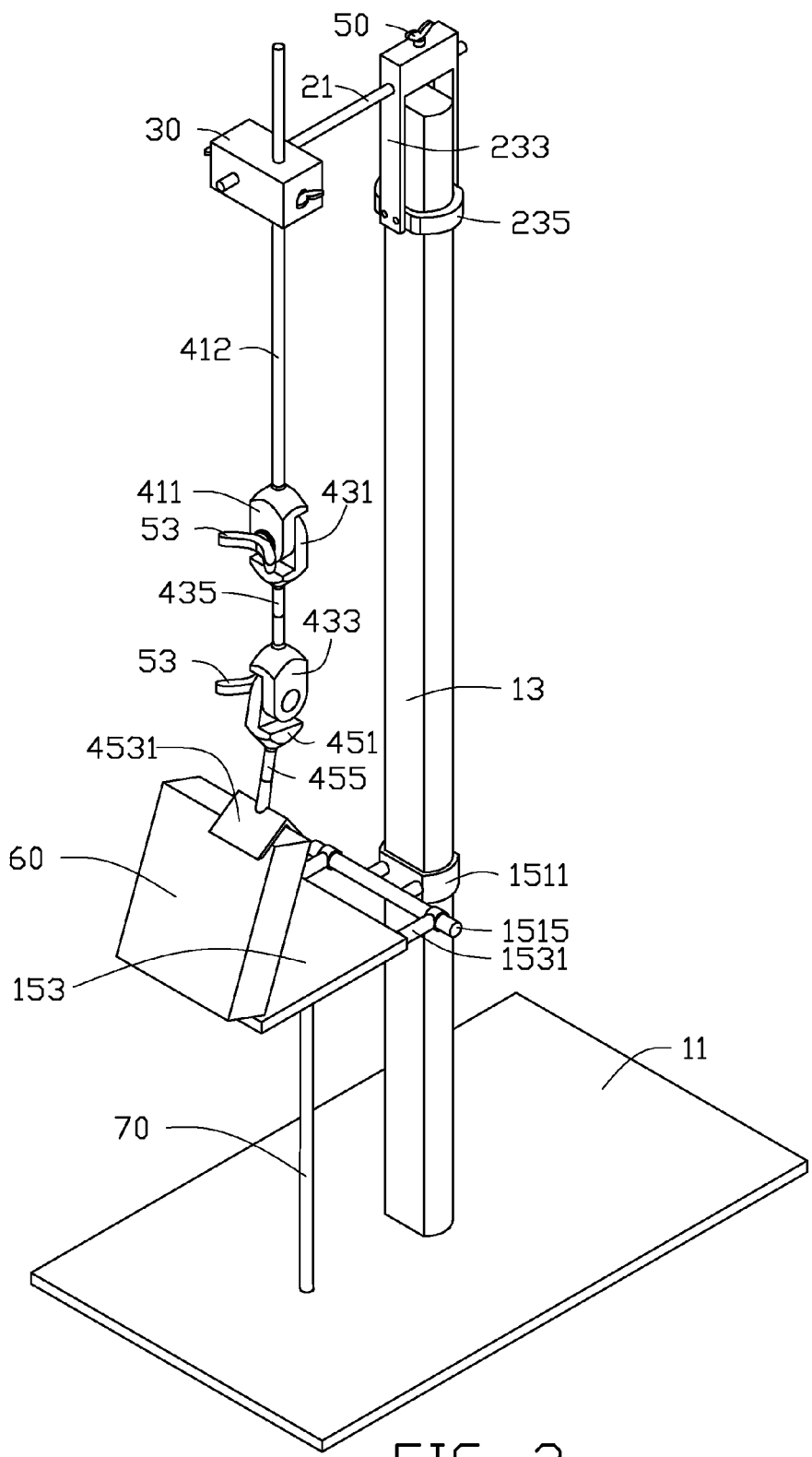
FIG. 3 is an assembled view of FIG. 1, showing a support member being in a first position.

Referring to FIG. 3, in assembly, the pivoting portion 431 abuts the first angle adjuster 411. The mounting hole 4311 of the pivoting portion 431 is aligned with the pivot hole 4112 of the first angle adjuster 411. A first pivoting pin 50 is mounted in the mounting hole 4311 and the pivot hole 4112 to pivotably mount the pivoting portion 431 and the first angle adjuster 411 together.

Then, the fixing portion 451 abuts the second angle adjuster 433. The fixing hole 4511 of the fixing portion 451 is aligned with the pivot slot 4332. A second pivoting pin 50 is inserted into the fixing hole 4511 and the pivot slot 4332, to mount the fixing portion 451 and the second angle adjuster 433 together. The pivoting pin 50 is secured on the securing member 20 and is rotated, to secure the securing member 20 to the pillar 13 firmly. The two pivoting pins 50 on the connecting member 30 are rotated, to firmly secure the post 21 and the first pole 412 together.

Figure 4:
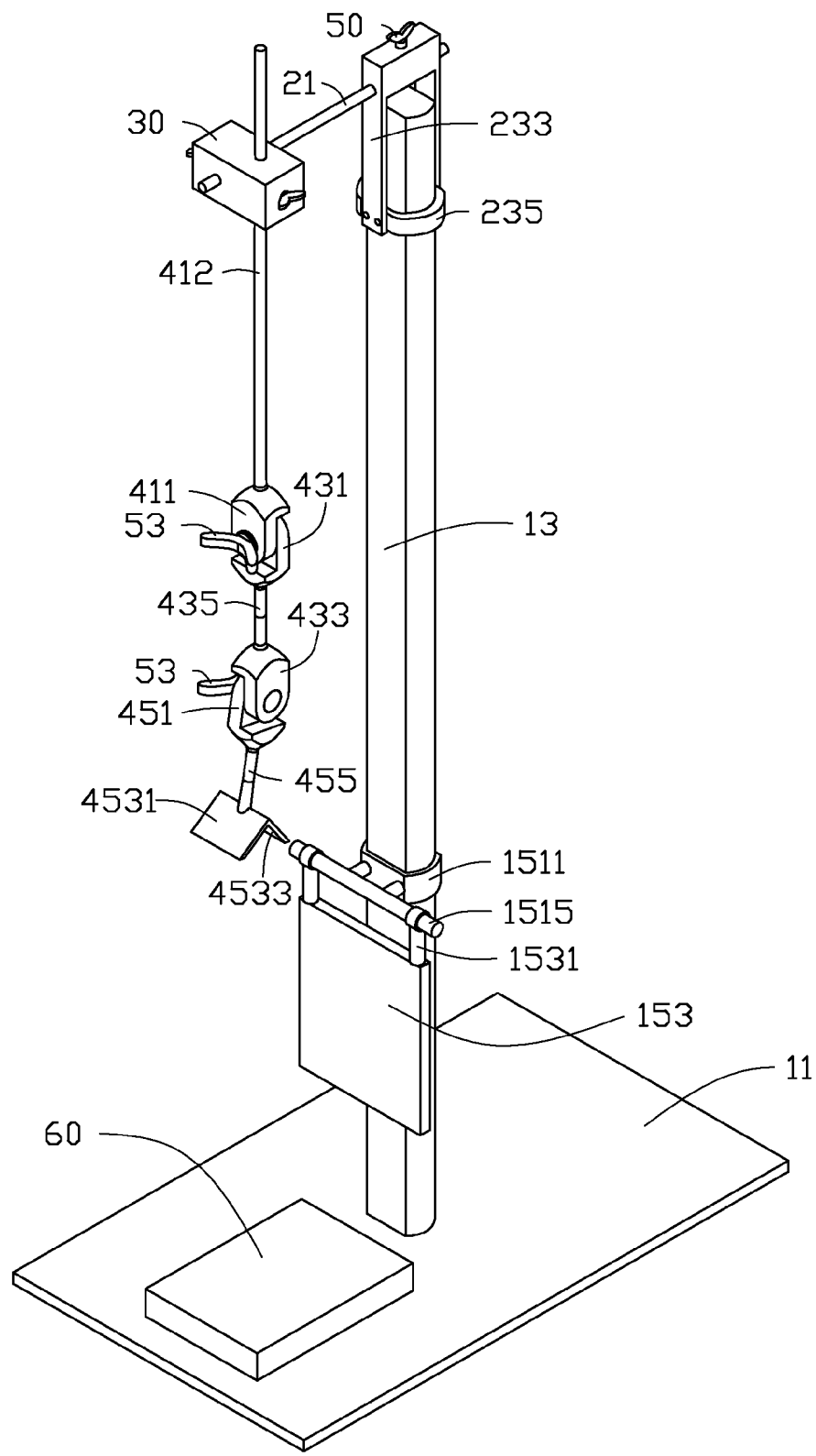
FIG. 4 is similar to FIG. 3, but shows the support member being in a second position.

Referring to FIGS. 3 and 4, the support plate 153 of the support member 15 can be rotated between in a first position, where the support plate 153 is substantially perpendicular to the pillar 13, and a second position, where the support plate 153 is substantially parallel to the pillar 13.

In use, a driving device 70 is (shown in FIG. 3) is attached to the bottom board 11, and power from the driving device 70 drives the support plate 153 to be moved to the first position. The first and second angle adjusters 411, 433 are rotated, adjusting the angle between the clamp member 453 and the support plate 153, and then the angle can be noted. A side plate of the product 60 is clamped between the first piece 4531 and the second piece 4533, and an arris of the product 60 abuts the support plate 153. The driving device 70 is quickly removed from the support plate 153. Then, the support plate 153 is rotated quickly to release the product 60 from the clamp member 453, until the support plate 153 is rotated to the second position. The product 60 drops. The arris of the product 60 strikes on the bottom board 11 or other surfaces. Therefore, the drop test device conveniently tests the arris of the product 60.

It is to be understood, however, that even though numerous characteristics and advantages have been set forth in the foregoing description of embodiments, together with details of the structures and functions of the embodiments, the disclosure is illustrative only and changes may be made in detail, especially in matters of shape, size, and arrangement of parts within the principles of the disclosure to the full extent indicated by the broad general meaning of the terms in which the appended claims are expressed.

What is claimed is:

1. A drop test device comprising:
   an operating platform comprising a pillar and a support member rotatably secured on the pillar, the support member comprising a fastening portion and a support plate, the fastening portion comprising a shaft; and two arms extends from the support plate, and the two arms are rotatably secured to the shaft; and
   a hanging mechanism, moveably mounted to the pillar, comprising a clamp member, a first part, a second part, a first angle adjuster, a third part, the clamp member being located above the support member, the first angle adjuster being located on the first part and configured to adjust an angle of the second part, the second part being located between the first part and the third part, the clamp member being disposed on the third part, the second part comprising a pivoting portion and a second angle adjuster, the pivoting portion being rotatably secured to the first angle adjuster, and the third part comprising a fixing portion secured to the second angle adjuster;
   wherein the support member is configured to move between a first configuration, where the support member is substantially perpendicular to the pillar, and a second configuration, where the support member is substantially parallel to the pillar, to have an arris of the product directed towards a surface.

2. The drop test device of claim 1, wherein the fastening portion further comprises a ring and a pin connected the ring, the ring surrounds the pillar, and the pin is connected the shaft.

3. The drop test device of claim 1, wherein a number of graduations are labeled on the first angle adjuster, and the number of graduations notes the angle of the second part.

4. The drop test device of claim 1, further comprising a frame secured to the pillar and a connecting member, the frame comprising a post moveably secured to the connecting member, the first part comprising a first pole connected to the first angle adjuster, and the first pole is secured to the connecting member.

5. The drop test device of claim 4, wherein the frame comprises a securing portion, two legs connected to the securing portion, and a loop connected to the two legs; and the loop surrounds the pillar.

6. The drop test device of claim 1, wherein the clamp member comprises a first piece and a second piece connected to the first piece, and the second piece is substantially perpendicular to the first piece.

7. A drop test device comprising:
   an operating platform comprising a pillar and a support member, the support member comprising a fastening portion attached to the pillar and a support plate rotatably secured to the fastening portion;
   a connecting member;
   a securing member moveably attached to the pillar and the connecting member;
   a hanging mechanism moveably secured to the connecting member, comprising a clamp member a first part, a second part, and a first angle adjuster, the clamp member being configured for positioning a product, the first angle adjuster being located on the first part and configured to adjust an angle of the second part; and
   a number of graduations labeled on the first angle adjuster and configured to note the angle of the second part;
   wherein the support plate is rotated between a first position and a second position, in the first position, the clamp member and the support member are configured to secure the product, and the support plate is substantially perpendicular to the pillar; in the second position, the support member is substantially parallel to the pillar, to have an arris of the product directed towards a surface.

8. The drop test device of claim 7, wherein the fastening portion further comprises a ring, a pin and a shaft, the ring surrounds the pillar, and the pin is connected the ring and the shaft.

9. The drop test device of claim 7, wherein the hanging mechanism further comprises a third part, the second part is located between the first part and the third part, and the clamp member is disposed on the third part, located above the support plate.

10. The drop test device of claim 7, wherein the first part comprises a first pole connected to the first angle adjuster, and the first pole secured to the connecting member.

11. The drop test device of claim 9, wherein the second part comprises a pivoting portion and a second angle adjuster, the pivoting portion is rotatably secured to the first angle adjuster, and the third part comprises a fixing portion secured to the second angle adjuster.

12. The drop test device of claim 7, further comprising a frame; the frame comprises a securing portion, two legs connected to the securing portion, and a loop connected to the two legs; and the loop surrounds the pillar.

13. The drop test device of claim 7, wherein the clamp member comprises a first piece and a second piece connected to the first piece, and the second piece is substantially perpendicular to the first piece.

14. A drop test device comprising:
   an operating platform comprising a pillar and a support member, the support member comprising a fastening portion attached to the pillar and a support plate rotatably secured to the fastening portion;

a connecting member;

a securing member moveably attached to the pillar and the connecting member; and a hanging mechanism moveably secured to the connecting member, comprising a clamp member a first part, a second part, and a first angle adjuster, the clamp member being configured for positioning a product, the first angle adjuster being located on the first part and configured to adjust an angle of the second part, the first part comprising a first pole connected to the first angle adjuster and secured to the connecting member;

wherein the support plate is rotated between a first position and a second position, in the first position, the clamp member and the support member are configured to secure the product, and the support plate is substantially perpendicular to the pillar; in the second position, the support member is substantially parallel to the pillar, to have an arris of the product directed towards a surface.

* * * * *